(12) United States Patent
Givens et al.

(10) Patent No.: US 8,115,029 B2
(45) Date of Patent: Feb. 14, 2012

(54) COBALT-CATALYZED OXIDATIONS IN VOLUMETRICALLY EXPANDED LIQUIDS BY COMPRESSED GASES

(75) Inventors: Richard S. Givens, Lawrence, KS (US); Chi Cheng Ma, Lawrence, KS (US); Daryle H. Busch, Lawrence, KS (US); Bala Subramaniam, Lawrence, KS (US); Bhuma Rajagopalan, Wilmington, DE (US)

(73) Assignee: University of Kansas, Lawrence, KS (US)

( * ) Notice: Subject to any disclaimer, the term of this patent is extended or adjusted under 35 U.S.C. 154(b) by 795 days.

(21) Appl. No.: 11/934,612

(22) Filed: Nov. 2, 2007

(65) Prior Publication Data

US 2008/0139841 A1 Jun. 12, 2008

Related U.S. Application Data

(60) Provisional application No. 60/856,147, filed on Nov. 2, 2006.

(51) Int. Cl.
*C07C 51/16* (2006.01)

(52) U.S. Cl. ........ 562/412; 562/407; 562/410; 562/422; 568/800

(58) Field of Classification Search .................. None
See application file for complete search history.

(56) References Cited

U.S. PATENT DOCUMENTS

| 3,562,318 A | 2/1971 | Barone et al. |
| 4,329,493 A | 5/1982 | Hashizume et al. |
| 4,593,122 A | 6/1986 | Hashizume et al. |
| 4,827,025 A | 5/1989 | Shiraki et al. |
| 4,835,307 A | 5/1989 | Lindahl et al. |
| 5,087,741 A | 2/1992 | Tennant et al. |
| 5,122,992 A | 6/1992 | Kompanek |
| 5,693,859 A | 12/1997 | Takase et al. |
| 5,760,288 A | 6/1998 | Asahi et al. |
| 5,981,420 A * | 11/1999 | Nakano et al. ............... 502/155 |
| 6,160,159 A | 12/2000 | Smith |
| 6,465,685 B1 * | 10/2002 | Phelps et al. ................. 562/422 |
| 6,740,785 B2 | 5/2004 | Subramaniam et al. |
| 2003/0100805 A1 * | 5/2003 | Subramaniam et al. ...... 568/959 |

FOREIGN PATENT DOCUMENTS

EP 0 754673 1/1997

OTHER PUBLICATIONS

Ma et al., "Real time ReactIR Studies of High pressure Oxidation of Arylalkanes", ACS PowerPoint, Presentation to the American Chemical Society, San Francisco CA, Sep. 13, 2006.

* cited by examiner

*Primary Examiner* — Sudhakar Katakam
(74) *Attorney, Agent, or Firm* — Stinson Morrison Hecker LLP

(57) ABSTRACT

Oxidations of hydrocarbons, cycloalkanes and alkenes, arylalkanes, and a variety of other organic substrates are accomplished by cobalt-N-hydroxysuccinimide co-catalyzed reactions with dioxygen under unusually mild, near ambient conditions of temperature and pressure. The improved safety of the oxidation method and the high yields of product obtained make use of a unique combination of cobalt (II) complexes with N-hydroxysuccinimide. These autoxidation reactions do not have prolonged initiation times. Many of these reactions can be safely performed under normal chemical laboratory conditions and do not require specialized equipment or reagents.

17 Claims, 1 Drawing Sheet

COBALT-CATALYZED OXIDATIONS IN VOLUMETRICALLY EXPANDED LIQUIDS BY COMPRESSED GASES

CROSS-REFERENCE TO RELATED APPLICATIONS

This application is based on and claims priority to U.S. Provisional Application Ser. No. 60/856,147, filed on Nov. 2, 2006, which is hereby incorporated by reference.

STATEMENT REGARDING FEDERALLY SPONSORED RESEARCH OR DEVELOPMENT

The present invention was supported in part by National Science Foundation Grant No. EEC-030689 and the federal government may have certain rights in the invention.

BACKGROUND OF THE INVENTION

1. Field of the Invention

The present invention is directed to the oxidation of hydrocarbons, especially cycloalkanes and alkenes, arylalkanes, and a variety of other organic substrates.

2. Description of Related Art

The oxidation of hydrocarbon substrates has traditionally been performed using the so-called Mid-Century Process ("MCP"). Terephthalic acid, for example, is prepared, as described in U.S. Pat. No. 2,833,816 issued to Mid Century Coloration in 1958, by the oxidation of para-xylene by air in acetic acid solvent, at around 200° C. and 200 psig pressure, in the presence of homogeneous, liquid phase catalysts comprising of cobalt, manganese, and bromine. Various modifications and improvements of this process are utilized for the manufacture of terephthalic and many other aromatic carboxylic acids. These processes are described in U.S. Pat. Nos. 5,693,856; 3,562,318A; 5,760,288; 6,160,159; 4,329,493; 4,593,122; 4,827,025; 4,835,307; 5,087,741; 5,112,992; EP 0 754,673 A. See generally U.S. Published Patent Application No. 2003/0050504. The present invention is directed an improved process for the oxidation of hydrocarbon substrates.

BRIEF SUMMARY OF THE INVENTION

In the present invention, oxidation of organic substrates such as alkanes, alkenes, cycloalkanes, cycloalkenes, alkyl aromatics (e.g., methyl, ethyl, and other alkyl benzenes, especially xylenes), aryl alcohols (e.g., benzyl alcohols), aryl aldehydes (e.g. benzaldehydes), aryl acids, or mixtures thereof as well as other aromatic compounds having CH bonds adjacent to the aromatic ring. For example, cyclohexane can be converted to adipic acid, ethyl benzene to acetophenone, cyclohexene to cyclohexenone and cyclohexenone epoxide, and p-xylene to terephthalic acid, o-xylene to phthalic acid, and m-xylene to isophthalic acid, all of which are produced on large scales by industry. The oxidation reactions are accomplished under unusually mild near ambient conditions of temperature and pressure, with air or dioxygen in the presence of an oxidation catalyst comprised of cobalt (preferably cobalt tetrahydrate $Co(OAc)_2 \cdot 4H_2O$ or "CAT") and the co-catalyst selected from the group consisting of N-hydroxysuccinimide ("NHSI"), N-hydroxyphthalimide ("NHPI"), and N-hydroxymaleimide ("NHMI"). These autoxidation reactions do not have prolonged initiation times. Many of these reactions can be safely performed under normal chemical laboratory conditions and do not require specialized equipment or reagents.

In another aspect, the oxidation methods are applied to other reactive hydrocarbons and substituted benzenes with other functional groups, including substituted toluenes (e.g., o, m, p-toluic acids, aldehydes, and benzyl alcohol) derivatives. Other oxidations that could be performed by this method would include oxidations of alkenes to epoxides and allyl alcohols, and other aryl and alkyl hydrocarbons to carboxylic acids, ketones, and/or alcohols.

The system is particularly attractive because it is readily adapted to any scale and, in many cases, requires no special apparatus or equipment. In addition to the potential for application in large scale industrial processes, this green methodology offers advantages to the specialty and fine chemical industries where batch scale reactions are routinely conducted, often with harmful and waste producing oxidants like chromium(IV), manganese(VII), and hypochlorite or chlorine dioxide. The combination of lower temperatures and pressures, green oxidant, and simple green catalyst leads to economically and environmentally beneficial methodologies potentially applicable to many oxidation systems, ranging from the laboratory to the grand scale of commodities. Further, the compressed-gas expanded solvent systems employed in the present invention are advantageous not only because such systems are safer and permit higher oxygen concentrations, but also reduces the amount of solvent destruction, referred to as acetic acid and p-xylene "burning," and product over-oxidation, in comparison with the MidCentury, Eastman, and Shell processes.

More challenging oxidations, such as those of linear and cyclic hydrocarbons, are readily achieved at moderately higher temperatures and/or pressures. Solvents for this process are preferably organic acids, specifically acetic acid, or carbon dioxide volumetrically expanded liquids ("CXLs"). Higher concentrations of oxygen can be employed safely in the latter solvent systems. Both batch and continuous flow reactions have been employed. The reactions are run at ambient temperatures or higher and at ambient pressure or higher to yield oxidation products such as acids, ketones, epoxides, and alcohols. In general, oxidations in $scCO_2$ and CXL as solvents are safer and, in cases like terephthalic acid, produce a finer particulate product, an advantage for purification processes.

Among the most notable features of the present invention are the extremely mild reaction conditions. For example, for many substrates oxidation can be performed at ambient temperature, i.e., at room temperature, and at atmospheric pressure with air (21% dioxygen) as the oxidant with a readily available catalyst, e.g., cobalt acetate, in combination with an initiator or co-catalyst, N-hydroxysuccinimide. The oxidations are rapid and high yielding, with few if any side products.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

Figure 1:
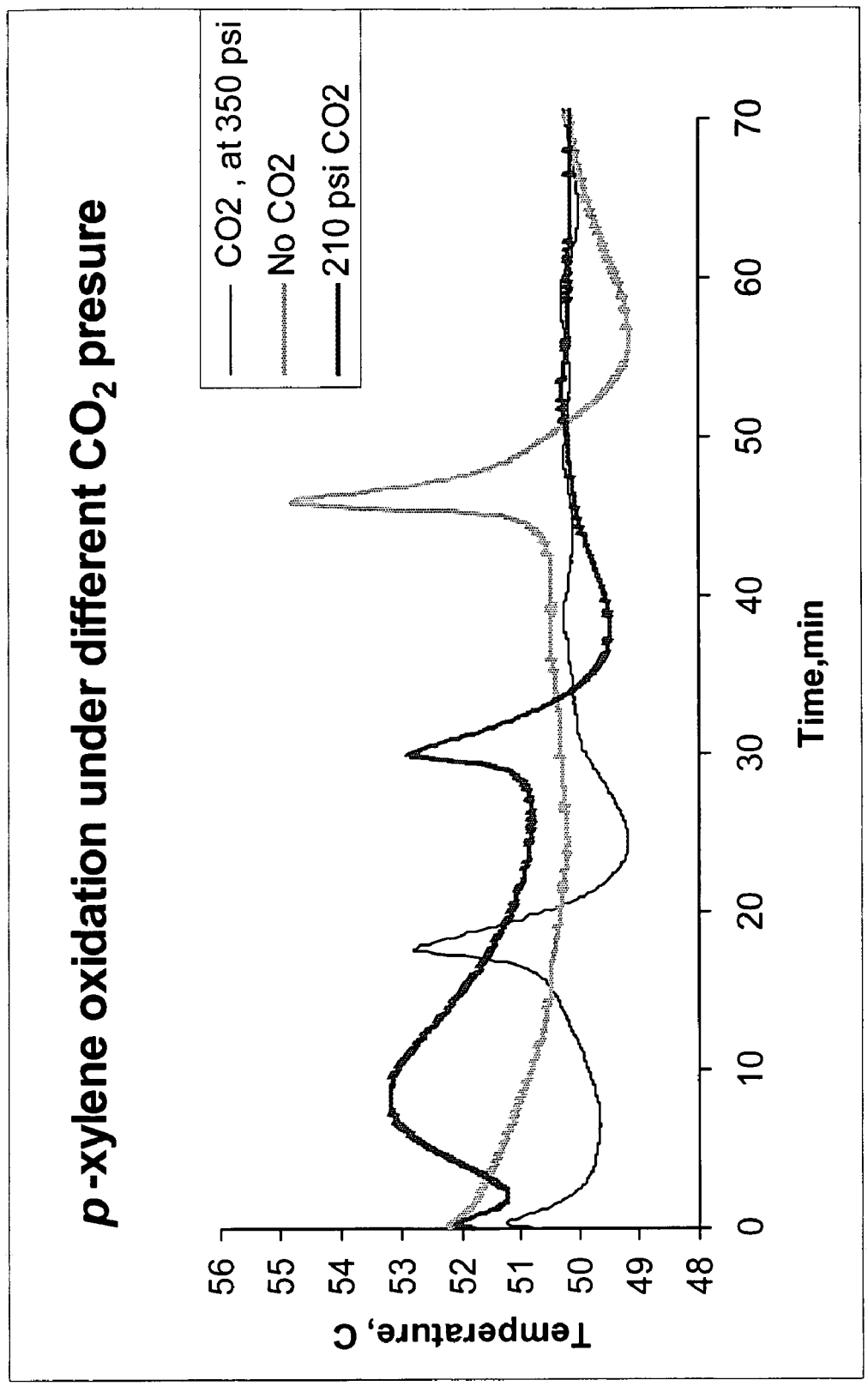
FIG. 1 shows para-xylene oxidation in which the solvent is volumetrically expanded with carbon dioxide at different pressures.

The present invention is directed to a process for oxidizing a hydrocarbon substrate comprising the steps of contacting the hydrocarbon substrate with a catalyst system comprising a cobalt catalyst and a co-catalyst selected from the group consisting of N-hydroxysuccinimide, N-hydroxyphthalimide, and N-hydroxymaleimide. The oxidation reaction preferably is performed in an organic solvent system, and most preferably with a solvent system that has been volumetrically expanded using a compressed gas.

A number of oxidizing agents can be used as required in the methods of the invention. The most common oxidation agents are selected from the group consisting of air, oxygen, ozone, $N_2O$, and mixtures thereof. Molecular oxygen (dioxygen) is the preferred agent.

In a preferred aspect, the cobalt catalyst comprises a cobalt carboxylate. Most preferred cobalt catalysts are selected from the group consisting of cobalt acetate tetrahydrate [Co(OAc)$_2$.4H$_2$O], anhydrous cobalt acetate [Co(OAc)$_2$], cobalt naphthenate, cobalt propionate, cobalt-2-ethylhexanoate, cobalt benzoylactonate, cobalt acetylacetone, cobalt stearate, and cobalt octanoate, and their hydrous and anhydrous forms.

The hydrocarbon substrate is preferably solubilized or dispersed in a solvent system. The solvent system preferably comprises an organic solvent system. In one aspect, the organic solvent system comprises an organic solvent selected from the group consisting of acetic acid, propionic acid, chloroacetic acid, dichloroacetic acid, trichloroacetic acid, trifluoroacetic acid.

In the present invention, the reaction mixture preferably comprises a sufficient quantity of a compressed gas to volumetrically expand the reaction mixture as generally taught by Subramaniam, et al., U.S. Pat. No. 6,740,785 titled "Catalytic oxidation of organic substrates by transition metal complexes in organic solvent media expanded by supercritical or sub-critical carbon dioxide" which is incorporated by reference. Preferred compressed gases are selected from the group consisting of carbon dioxide, $N_2O$, xenon, $SF_6$, and other light hydrocarbon gases (e.g., $C_4$ or less), such as propylene and ethylene, and mixtures thereof. The volumetric expansion is normally carried out by introducing a compressed gas into the reaction mixture. If the inert gas is also an oxidizing agent for the substrate (e.g., when $N_2O$ is employed), the oxidation reaction proceeds. However, where an inert gas such as $CO_2$ is employed, a separate oxidizing agent is introduced into the expanded reaction mixture to initiate the oxidation reaction.

The reaction mixture is preferably maintained and oxidation reaction preferably occurs at mild pressures. Typically the pressure range between about 10 and 250 bar, more preferably between about 10 and 100 bar, and most preferably between about 10 and 50 bar. In another aspect, the reaction mixture is maintained at a pressure which is less than about 250 bar, 150 bar, 100 bar, 80 bar, 90 bar, 70 bar, 60 bar, 50 bar, 40 bar, 30 bar, 20 bar, or 10 bar.

The reaction mixture is preferably maintained and the oxidation reaction preferably occurs at mild temperatures. Typically, the temperature ranges between about 20 and 250° C., more preferably between about of about 30 and 120° C., and still more preferably between about 30 to 70° C. Preferably, the temperature of the reaction mixture is between about 20 and 250° C., more preferably between about of about 20 and 80° C., and still more preferably between about 20 to 30° C. when the oxidizing agent is introduced into the reaction mixture. In another aspect, the initial temperature of the reaction mixture is less than about 250° C., 200° C., 150° C., 100° C., 90° C., 80° C., 70° C., 60° C., 40° C., or 30° C.

The oxidizable hydrocarbon substrates are preferably selected from the group consisting of one or more alkanes, alkenes, cycloalkanes, cycloalkenes, alkyl aromatics, aryl aldehydes, aryl carboxylic acids, aryl alcohols, or mixtures thereof.

As used herein, "alkane" embraces straight chain or branched aliphatic hydrocarbons. Representative straight chain alkanes include methane, ethane, propane, butane, pentane, hexane, heptane, octane, nonane, and decane. Representative branched alkanes include isobutane, isopentane, neopentane, 2-methylbutane, 2-methylpentane, 3-methylpentane, 2,2-dimethylbutane, 2,3-dimethylbutane, 3,3-dimethylbutane, 2-methylhexane, 3-methylhexane, 3,3-dimethylhexane, and 3,3-dimethylheptane. Preferred alkanes have 1 to 30 carbons. The alkanes may be optionally substituted with one or more halogen, hydroxyl, alkoxy (with $C_1$ to $C_6$ alkoxy being most preferred), amino, or carboxyl groups.

The term "alkene" embraces unsaturated hydrocarbons analogous in length and possible substitution to the alkanes described above, but that contain at least one double bond. Representative straight chain and branched alkenes include ethene, propene, butene, 2-butene, isobutene, 1-pentene, 2-pentene, 3-methyl-1-butene, 2-methyl-2-butene, 2,3-dimethyl-2-butene, 1-hexene, 2-hexene, 3-hexene, 1-heptene, 2-heptene, 3-heptene, 1-octene, 2-octene, 3-octene, 1-nonene, 2-nonene, 3-nonene, 1-decene, 2-decene, 3-decene, and the like. The alkenes may be optionally substituted with one or more halogen, hydroxyl, alkoxy (with $C_1$ to $C_6$ alkoxy being most preferred), amino, or carboxyl groups.

The term "cycloalkane," embraces a cyclic alkane. Exemplary cycloalkanes include cyclopentane, cyclohexane, cycloheptane, cyclooctane, cyclononane, and cyclodecane. The phrase also encompasses bicycloalkanes and tricycloalkanes. The cycloalkanes may be optionally substituted with one or more halogen, hydroxyl, alkyl, alkoxy (with $C_1$ to $C_6$ alkoxy being most preferred), amino, or carboxyl groups.

The term "cycloalkene" embraces a non-aromatic cyclic hydrocarbon having at least one carbon-carbon double bond in the cyclic system. Exemplary cycloalkenes include cyclopentene, cyclopentadiene, cyclohexene, cyclohexadiene, cycloheptene, cycloheptadiene, cycloheptatriene, cyclooctene, cyclooctadiene, cyclooctatriene, cyclooctatetraene, cyclononene, cyclononadiene, cyclodecene, cyclodecadiene, and the like. The cycloalkenes may be optionally substituted with a halogen. The cycloalkenes may be optionally substituted with one or more halogen, hydroxyl, alkyl, alkoxy (with lower C1 to C6 lower alkoxy being most preferred), amino, or carboxyl groups.

The term "alkyl aromatic" embraces an aromatic ring system substituted with an alkyl group. Exemplary alkyl aromatic compounds are alkyl benzenes, such as methyl benzene (toluene), ethyl benzene, propyl benzene, isopropylbenzene (cumene), 1,2-dimethylbenzene (o-xylene), 1,3-dimethylbenzene (m-xylene), 1,4-dimethylbenzene (p-xylene), 1,3,5-trimethylbenzene (mesitylene), 1,2,3-trimethylbenzene (hemimellitene), 1,2,4-trimethyl benzene (pseudocumene), 1,2,4,5-tetramethylbenzene (durene), 1,2,3,5-tetramethylbenzene (isodurene), 1-methyl-4-(1-methylethyl)benzene (cymene), butylbenzene, 1,2-diethylbenzene, 1,3-diethylbenzene, 1,4-diethylbenzene, 1,3,5-triethylbenzen, 1,2,3-triethylbenzene, 1,2,4-triethylbenzene, 1-methyl-2-ethylbenzene, 1-methyl-3-ethylbenzene, 1-methyl-4-ethylbenzene, 1-methyl-2-propylbenzene, 1-methyl-3-propylbenzene, 1-methyl-4-propylbenzene, 1-ethyl-2-propylbenzene, 1-ethyl-3-propylbenzene, 1-ethyl-4-propylbenzene, 1-methyl-2-butylbenzene, 1-methyl-3-butylbenzene, 1-methyl-4-butylbenzene, pentylbenzene, hexylbenzene, heptylbenzene, octylbenzene, nonylbenzene, dodecylbenzene, pentadecylbenzene, hexyltoluene, nonyltoluene, dodecyltoluene, and pentadecyltoluene. Other alkyl aromatics include 1-methylnaphthalene, 2-methylnaphthalene, 1,2-dimethylnaphthalene, 1,4-dimethylnaphthalene, 1,5-dimethylnaphthalene, 1,6-dimethylnaphthalene 1,7-dimethylnaphthalene, 1,8-dimethylnaphthalene, 1-ethylnaphthalene, 2,3-dimethylanthracene, 9-ethylanthracene, 2-methylanthracene, 1-methylanthracene, 9,10-dimethylphenanthrene, and 3-methylphenanthrene. The "aryl aromatics" may be optionally substituted with one or more halogen, hydroxyl, alkoxy (with lower $C_1$ to $C_6$ lower alkoxy being most preferred), amino, or carboxyl groups. Of these, alkyl aromatic compounds substituted with a halogen, for example, 1,2-dimethyl-4-chlorobenzene, are most preferred.

The term "aryl alcohol" embraces an aromatic ring substituted with one hydroxyl (—OH) containing alkyl moiety. Examples of aryl alcohols include benzyl alcohol, 1-phenylethanol, 2-phenylethanol, and 1-phenyl-2-propanol. Most preferred are benzyl alcohols, such as 4-methylbenzyl alcohol, 3-methylbenzyl alcohol, and 2-methylbenzyl alcohol. The "aryl alcohols" may be optionally substituted with one or more halogen, alkyl, alkoxy (with $C_1$ to $C_6$ alkoxy being most preferred), amino, or carboxyl groups.

The term "aryl aldehyde" embraces an aromatic compound substituted with at least one —CHO radical, such as benzaldehyde, 2-methylbenzaldehyde, 3-methylbenzaldehyde, 4-methylbenzaldehyde, and the like. The "aryl aldehydes" may be optionally substituted with one or more halogen, alkyl, alkoxy (with $C_1$ to $C_6$ alkoxy being most preferred), amino, or carboxyl groups.

An "aryl acid" or "aryl carboxylic acid" embraces aromatic compound substituted with at least one carboxylic acid (—COOH) radical. Suitable aryl acids include, for example, benzoic acid, o-toluic acid, m-toluic acid, p-toluic acid, 2-ethylbenzoic acid, 3-ethylbenzoic acid, 4-ethylbenzoic acid, 4-isopropylbenzoic acid, 4-tertiary butylbenzoic acid, 4-(1-methylpropyl)benzoic acid, and the like. Other aryl acids include those based on naphthalene or anthracene, such as 1-naphthoic acid, and 2-naphthoic acid. The aryl acids may optionally be substituted with a halogen, for example, 2-chlorobenzoic acid, 3-chlorobenzoic acid, 4-chlorobenzoic acid, 2,3-dibromobenzoic acid, 2,4-di-iodobenzoic acid, 2,6-dibromobenzoic acid, 3,4-dibromobenzoic acid, 3,5-dichlorobenzoic acid, 2,3,5-tribromobenzoic acid, 2,4,6-trichlorobenzoic acid, 2,3,4,5,6-pentabromobenzoic acid, and the like. The "aryl acids" may be optionally substituted with one or more halogen, alkyl, alkoxy (with $C_1$ to $C_6$ alkoxy being most preferred), or amino groups.

The term "alkyl" embraces a branched or unbranched saturated hydrocarbon group of 1 to 30 carbon atoms, analogous to the alkanes referenced. "Alkyl" embraces methyl, ethyl, n-propyl, isopropyl, n-butyl, isobutyl, t-butyl, octyl, decyl, tetradecyl, hexadecyl, eicosyl, tetracosyl, and the like. Preferred "alkyl" groups herein contain 1 to 12 carbon atoms. Most preferred are "lower alkyl" which refers to an alkyl group of 1 to 6, more preferably 1 to 4, carbon atoms.

The term "alkoxy" embraces oxy-containing groups substituted with an alkyl, or cycloalkyl group. Examples include, without limitation, methoxy, ethoxy, tert-butoxy, and cyclohexyloxy. Most preferred are "lower alkoxy" groups having one to six carbon atoms. Examples of such groups include methoxy, ethoxy, propoxy, butoxy, isopropoxy, and tert-butoxy groups.

The term "amino" embraces a primary, secondary or tertiary amino group of the formula —NR'R" wherein R' and R" as used in this definition are independently hydrogen, alkyl, aryl or other amino (in the case of hydrazine) or R' and R" together with the nitrogen atom to which they are attached, form a ring having 4-8 atoms. Thus, the term "amino," as used herein, includes unsubstituted, monosubstituted (e.g., monoalkylamino or monoarylamino), and disubstituted (e.g., dialkylamino or arylalkylamino) amino groups. Amino groups include —$NH_2$, methylamino, ethylamino, dimethylamino, diethylamino, methyl-ethylamino, pyrrolidin-1-yl, or piperidino, morpholino, etc. Other exemplary "amino" groups forming a ring include pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, quinolizinyl. The ring containing the amino group may be optionally substituted with another amino, alkyl, alkenyl, alkynyl, halo, or hydroxyl group.

The term "aromatic" or "aryl" embraces organic cyclic compound where all the atoms in the ring(s) are saturated and/or conjugated. The term includes two or more fused aromatic rings, preferably made up of carbon and hydrogen atoms. The term "fused" means that a second ring is present (i.e., attached or formed) by having two adjacent atoms in common (i.e., shared) with the first ring. The term "fused" is equivalent to the term "condensed." The term includes benzenoid aromatics, which are cyclic compounds made up of one or more benzene like rings in which the Pi electrons are conjugated. Examples are benzene, napthalene, phenanthrene, anthracene, and pyridine.

The term "halogen" or "halo" as used herein embraces a fluorine, chlorine, bromine, or iodine atom.

The term "hydroxy" or "hydroxyl" embraces the substituent —OH.

The term "carboxyl" embraces the group —R'C(=O)OR", wherein R' and R" as used in this definition are independently hydrogen, alkyl, or R' can additionally be a covalent bond. "Carboxyl" includes both carboxylic acids, and carboxylic acid esters. The term "carboxylic acid" refers to a carboxyl group in which R" is hydrogen. Such acids include formic, acetic, propionic, butyric, valeric acid, and 2-methyl propionic acid. The term "carboxylic acid ester" or "ester" refers to a carboxyl group in which R" is alkyl.

The term "induction period" or "oxidation induction time" ("OIT") is the time delay after mixing all reagents that is required for the initiation of reaction. This delay time may be very short, a few minutes, or long, up to 48 hours, before the oxidation reaction commences.

The terms "optional" or "optionally" mean that the subsequently described event or circumstance may or may not occur, and that the description includes instances where said event or circumstance occurs and instances in which it does not. "Optionally" is inclusive of embodiments in which the described condition is present and embodiments in which the described condition is not present. For example, "optionally substituted phenyl" means that the phenyl may or may not be substituted, and that the description includes both unsubstituted phenol and phenol wherein there is substitution. "Optionally" is inclusive of embodiments in which the described conditions is present and embodiments in which the described condition is not present.

The following examples set forth preferred methods in accordance with the invention. It is to be understood, however, that these examples are provided by way of illustration and nothing therein should be taken as a limitation upon the overall scope of the invention.

Example 1

Oxidation of p-Xylene Using CAT and NHSI at 21° C.

In this example, a solution of 0.076 g (0.3 mmol) of cobalt acetate tetrahydrate ("CAT"), 0.5474 g (5.2 mmol) of p-xylene and 0.1168 g (1.0 mmol) N-hydroxysuccinimide ("NHSI") was prepared in 40 ml of acetic acid at 21° C. in a Parr Hastelloy reactor fitted with temperature and pressure controllers. 302 psi of $CO_2$ was slowly introduced into the reactor, then 300 psi pure oxygen was charged into the reactor. The mixture was stirred under pressure for 24 hours at 21° C., after which the pressure was released. A rapid pressure decrease (due to consumption of $O_2$ in the liquid phase reaction) after an induction period of 398 minutes indicated rapid reaction. These profiles are steep and level off within 30 minutes after induction. The white solid of terephthalic acid ("TPA") was filtered, and the filtrate analyzed by HPLC using biphenyl as the internal standard. The solid TPA product was washed with additional acetic acid (20 ml) and dried in an oven at 120° C. for six hours to obtained 0.58 g of TPA (yield: 68% based on the initial moles of p-xylene consumed).

Example 2

Oxidation of p-Xylene Using CAT and NHSI at 100° C.

In this example, a solution of 0.1158 g (1.01 mmol) of N-hydroxysuccinimide, 0.5199 g (4.9 mmol) of p-xylene and 0.1273 g (0.511 mmol) CAT in 40 ml of acetic acid was heated to 100° C. in a Parr Hastelloy reactor fitted with temperature and pressure controllers. After the temperature reached 100° C., 860 psi of air was slowly introduced into the reactor. The mixture was stirred under pressure for one hour at 100° C., the pressure was released, and the mixture cooled to room temperature. Within roughly 15 minutes following $O_2$ introduction, a rapid temperature rise occurred (due to heat generated by the exothermic oxidation) accompanied by a drop in reactor pressure (due to consumption of $O_2$ in the liquid phase reaction) indicating rapid reaction. These profiles are steep and level off within minutes after induction (typical T and P profiles will be provided in the patent application). The white solid of terephthalic acid (TPA) was filtered, and the filtrate analyzed by HPLC using biphenyl as the internal standard. The solid TPA product was washed with additional acetic acid (20 ml) and dried in an oven at 120° C. for six hours to obtain 0.795 g of TPA (yield: 98% based on the initial moles of p-xylene reacted). Analysis: 97.7% TPA, 2.0% carboxybenzaldehyde (CBA), and 0.3% p-toluic acid (PTA).

Example 3

Oxidation of p-Xylene Using CAT and NHSI at 60° C.

In this example, a solution of 0.1208 g (1.05 mmol) of N-hydroxysuccinimide, 0.5291 g (4.99 mmol) of p-xylene and 0.1142 g (0.46 mmol) of CAT in 40 ml of acetic acid was heated to 60° C. in a Parr Hastelloy reactor with temperature and pressure transducer. After the temperature reached 60° C., 233 psi of air was slowly introduced into the reactor. The mixture was stirred under pressure for one hour at 60° C., then the pressure was released, and the mixture was cooled to room temperature. A rapid temperature rise (due to heat generated by the exothermic oxidation) within roughly 20 minutes following $O_2$ introduction, accompanied by a drop in reactor pressure (due to consumption of $O_2$ in the liquid phase reaction) indicated rapid reaction. The white solid TPA was filtered, and the filtrate analyzed by HPLC using biphenyl as the internal standard. The solid TPA product was washed with acetic acid (20 ml) and dried in an oven at 120° C. for six hours to yield TPA (0.75 g, 95%). Analytical solid component results: 96.4% TPA, 0.78% CBA, and 2.81% PTA.

Example 4

Oxidation of p-Xylene Using CAT and NHSI at 60° C.

In this example, a solution of 0.1168 g (1.01 mmol) of N-hydroxysuccinimide, 0.5348 g (5.05 mmol) p-xylene and 0.0756 g (0.3 mmol) of CAT in 40 ml of acetic acid was heated to 60° C. in a Parr Hastelloy reactor with a temperature and pressure transducer. After the temperature reached 60° C., 506 psi of $CO_2$ was introduced to the reactor, then 350 psi of $O_2$ was slowly added to the reactor. A rapid temperature rise (due to heat generated by the exothermic oxidation) within roughly six minutes following $O_2$ introduction, accompanied by a drop in reactor pressure (due to consumption of $O_2$ in the liquid phase reaction) indicated rapid reaction after induction. These profiles are steep and level off within minutes after induction. The mixture was stirred under pressure for one hour at 60° C., then cooled to room temperature after releasing the pressure. The white solid TPA was filtered, the filtrate analyzed by HPLC using biphenyl as an internal standard. The solid TPA product was washed by acetic acid (20 ml) and dried in an oven at 120° C. for six hours to yield TPA (0.75 g, 89.2%). A similar product analysis was found, see example 2.

Example 5

Oxidation of p-Xylene Using Anhydrous Cobalt Acetate and NHSI at 60° C.

In this example, a solution of 0.1168 g (1.01 mmol) of N-hydroxysuccinimide, 0.5256 g (4.96 mmol) p-xylene and 0.078 g (0.3 mmol) of $Co(acac)_2$ in 40 ml of acetic acid was heated to 60° C. in a Parr Hastelloy reactor with a temperature and pressure transducer. After the temperature reached 60° C., 614 psi of $CO_2$ was introduced to the reactor, then 340 psi of $O_2$ was slowly added to the reactor. The mixture was stirred under pressure for one hour at 60° C., then cooled to room temperature after releasing the pressure. A rapid temperature rise (due to heat generated by the exothermic oxidation) within roughly six minutes following $O_2$ introduction, accompanied by a drop in reactor pressure (due to consumption of $O_2$ in the liquid phase reaction) indicates rapid reaction after induction. The white solid TPA was filtered, the filtrate was analyzed by HPLC using biphenyl as the internal standard. The solid TPA product was washed with acetic acid (20 ml) and dried in an oven at 120° C. for six hours to yield TPA (0.75 g, 74%). The product analysis was similar to that given in Example 2.

Example 6

Oxidation of p-Xylene Using CAT and NHSI at 80° C.

In this example, a solution of 0.1032 g (0.9 mmol) of N-hydroxysuccinimide, 0.5165 g (4.87 mmol) p-xylene, 0.1137 g (0.46 mmol) of CAT and 0.0591 g (0.12 mmol) of Zr(acac)$_4$ in 40 ml of acetic acid was heated to 80° C. in a Parr Hastelloy reactor with a temperature and pressure transducer. After the temperature reached 80° C., 580 psi of CO$_2$ was introduced into the reactor, then 360 psi of O$_2$ was slowly added to the reactor. A rapid temperature rise (due to heat generated by the exothermic oxidation) within roughly three minutes following O$_2$ introduction, accompanied by a drop in reactor pressure (due to consumption of O$_2$ in the liquid phase reaction) indicates rapid reaction induction. These profiles are steep and level off within minutes after induction. The mixture was stirred under pressure for one hour at 80° C., then cooled to room temperature after releasing the pressure. The white solid of TPA was filtered, and the filtrate analyzed by HPLC using biphenyl as the internal standard. The solid TPA product was washed with extra acetic acid (20 ml) and dried in an oven at 120° C. for six hours to yield TPA (0.75 g, 26%). A product analysis was similar to that obtained in Example 2.

Example 7

Oxidation of p-Xylene Using CAT and NHSI at 60° C.

In this example, a solution of 0.0562 g (0.49 mmol) of N-hydroxysuccinimide, 0.5438 g (5.13 mmol)$_p$-xylene, 0.0601 g (0.24 mmol) of CAT in 40 ml of acetic acid was heated to 60° C. in a Parr Hastelloy reactor with temperature and pressure transducer. After the temperature reached 60° C., 200 psi of CO$_2$ was introduced into the reactor, then 450 psi of O$_2$ was slowly added to the reactor. The mixture was stirred under pressure for one hour at 60° C., then cooled to room temperature after releasing the pressure. A rapid temperature rise (due to heat generated by the exothermic oxidation) within roughly one minute following O$_2$ introduction, accompanied by a drop in reactor pressure (due to consumption of O$_2$ in the liquid phase reaction) indicates rapid reaction induction. These profiles are steep and level off within minutes after induction. The white solid of TPA was filtered, and the filtrate analyzed by HPLC using biphenyl as the internal standard. The solid TPA product was washed with acetic acid (20 ml) and dried in the oven at 120° C. for six hours to obtain TPA (0.23 g, 27%).

Example 8

Oxidation of p-Xylene Using CAT and NHSI at 30° C.

In this example, a solution of 0.1168 g (1.01 mmol) of N-hydroxysuccinimide, 0.5358 g (5.05 mmol) p-xylene, 0.076 g (0.30 mmol) of CAT in 40 ml of acetic acid was heated to 30° C. in a Parr Hastelloy reactor with a temperature and pressure transducer. After the temperature reached 30° C., 537 psi of CO$_2$ was introduced to the reactor, then 340 psi of O$_2$ was slowly added to the reactor. The mixture was stirred under pressure for 12 hours at 30° C., then cooled to room temperature after releasing the pressure. A rapid temperature rise (due to heat generated by the exothermic oxidation) within roughly 140 minutes following O$_2$ introduction, accompanied by a drop in reactor pressure (due to consumption of O$_2$ in the liquid phase reaction) indicated rapid reaction after induction. These profiles are steep and level off within minutes after induction. The white solid of TPA was filtered and the filtrate was analyzed by HPLC using biphenyl as the internal standard. The solid TPA product was washed with acetic acid (20 ml) and dried in the oven at 120° C. for six hours to yield TPA (0.23 g, 76%).

Example 9

Oxidation of p-Xylene Using CAT and NHSI at 21° C.

In this example, a solution of 0.1168 g (1.01 mmol) of N-hydroxysuccinimide, 0.5471 g (5.05 mmol) p-xylene, 0.076 g (0.30 mmol) of CAT in 40 ml of acetic acid was heated to 21° C. in a Parr Hastelloy reactor with a temperature and pressure transducer. After the temperature reached 21° C., 302 psi of CO$_2$ was introduced into the reactor, then 429 psi of O$_2$ was slowly added to the reactor. The mixture was stirred under pressure or 12 hours at 21° C., then cooled to room temperature after releasing the pressure. A rapid temperature rise (due to heat generated by the exothermic oxidation) within roughly 170 minutes following O$_2$ introduction, accompanied by a drop in reactor pressure (due to consumption of O$_2$ in the liquid phase reaction) indicated rapid reaction induction. These profiles are steep and level off within minutes after induction. The white solid of TPA was filtered and the filtrate analyzed by HPLC using biphenyl as the internal standard. The solid TPA product was washed with acetic acid (20 ml) and dried in the oven at 120° C. for six hours to yield TPA (0.57 g, 67%).

Example 10

Oxidation of p-Xylene Using CAT and NHPI

In this example, a solution of 0.1648 g (1.01 mmol) of N-hydroxyphthalimide ("NHPI"), 0.5200 g (4.9 mmol) of p-xylene and 0.1273 g (0.511 mmol) cobalt acetate tetrahydrate in 40 ml of acetic acid was heated to 100° C. in a Parr Hastelloy reactor fitted with temperature and pressure controllers. After the temperature reached 100° C., 860 psi of air was slowly introduced into the reactor. The mixture was stirred under pressure for one hour at 100° C., the pressure was released, and the mixture cooled to room temperature. Within roughly 15 minutes following O$_2$ introduction, a rapid temperature rise occurred (due to heat generated by the exothermic oxidation) accompanied by a drop in reactor pressure (due to consumption of O$_2$ in the liquid phase reaction) indicating rapid reaction. These profiles are steep and level off within minutes after induction. The white solid of terephthalic acid (TPA) was filtered, and the filtrate analyzed by HPLC using biphenyl as the internal standard. The solid TPA product was washed with additional acetic acid (20 ml) and dried in an oven at 120° C. for six hours to obtain, 26% TPA and 71% PTA.

Example 11

Oxidation of p-Xylene Using CAT and NHMI

In this example, a solution of 0.1140 g (1.01 mmol) of N-hydroxymaleimide ("NHMI"), 0.5201 g (4.9 mmol) of p-xylene and 0.1273 g (0.511 mmol) cobalt acetate tetrahydrate in 40 ml of acetic acid was heated to 60° C. in a Parr Hastelloy reactor fitted with temperature and pressure controllers. After the temperature reached 60° C., 860 psi of air was slowly introduced into the reactor. The mixture was stirred under pressure for one hour at 60° C., the pressure was released, and the mixture cooled to room temperature. Within roughly 15 minutes following O$_2$ introduction, a rapid temperature rise occurred (due to heat generated by the exothermic oxidation) accompanied by a drop in reactor pressure (due to consumption of $O_2$ in the liquid phase reaction) indicating rapid reaction. These profiles are steep and level off within minutes after induction. The white solid of terephthalic acid (TPA) was filtered, and the filtrate analyzed by HPLC using biphenyl as the internal standard. The solid TPA product was washed with additional acetic acid (20 ml) and dried in an oven at 120° C. for six hours. Product analysis: 32% TPA, and 65% p-toluic acid ("PTA").

Example 12

Oxidation of m-Xylene Using CAT and NHSI

In this example, a solution of 0.1196 g (1.04 mmol) of N-hydroxysuccinimide, 0.5247 g (4.94 mmol) of m-xylene and 0.1263 g (0.51 mmol) of CAT in 40 ml of acetic acid was heated to 60° C. in a Parr Hastelloy reactor with temperature and pressure transducer. After the temperature reached 60° C., 233 psi of air was slowly introduced into the reactor. The mixture was stirred under pressure for one hour at 60° C., then the pressure was released, and the mixture was cooled to room temperature. A rapid temperature rise (due to heat generated by the exothermic oxidation) within roughly 20 minutes following $O_2$ introduction, accompanied by a drop in reactor pressure (due to consumption of $O_2$ in the liquid phase reaction) indicated rapid reaction. The white solid was filtered, and the filtrate analyzed by HPLC using biphenyl as the internal standard. The solid product was washed with acetic acid (20 ml) and dried in an oven at 120° C. for six hours to yield isophthalic acid (80%).

Example 13

Oxidation of o-Xylene Using CAT and NHSI

In this example, a solution of 0.1117 g (0.9705 mmol) of N-hydroxysuccinimide, 0.5199 g (4.90 mmol) of o-xylene and 0.1251 g (0.50 mmol) of CAT in 40 ml of acetic acid was heated to 60° C. in a Parr Hastelloy reactor with temperature and pressure transducer. After the temperature reached 60° C., 233 psi of air was slowly introduced into the reactor. The mixture was stirred under pressure for one hour at 60° C., then the pressure was released, and the mixture was cooled to room temperature. A rapid temperature rise (due to heat generated by the exothermic oxidation) within roughly 20 minutes following $O_2$ introduction, accompanied by a drop in reactor pressure (due to consumption of $O_2$ in the liquid phase reaction) indicated rapid reaction. The white solid was filtered, and the filtrate analyzed by HPLC using biphenyl as the internal standard. The solid product was washed with acetic acid (20 ml) and dried in an oven at 120° C. for six hours to yield phthalic acid (75%).

Example 14

Oxidation of Ethylbenzene Using CAT and NHSI

In this example, a solution of 0.1158 g (1.01 mmol) of N-hydroxysuccinimide, 0.544 g (5.13 mmol) of ethylbenzene and 0.1158 g (0.46 mmol) of cobalt acetate tetrahydrate in 40 ml of acetic acid was heated to 30° C. in a Parr Hastelloy reactor with temperature and pressure transducer. After the temperature reached 30° C., 233 psi of air was slowly introduced to the reactor. The mixture was stirred under pressure for one hour at 30° C., then the pressure was released, and the mixture was cooled to room temperature. A slow temperature rise (due to heat generated by the exothermic oxidation) within roughly 30 minutes following $O_2$ introduction, accompanied by a drop in reactor pressure (due to consumption of $O_2$ in the liquid phase reaction) indicates rapid reaction following induction. These profiles are steep and level off within minutes after induction. The reaction product mixture was extracted by ethyl acetate, then washed by water and saturated NaCl, dried over $Na_2SO_4$ to give acetophenone 80% and starting material 20% analysis by GC-MS and HPLC.

Example 15

Oxidation of Cyclohexane Using CAT and NHSI

In this example, a solution of 0.1191 g (1.03 mmol) of N-hydroxysuccinimide, 1.0074 g (9.5 mmol) of cyclohexane and 0.1330 g (0.53 mmol) of cobalt acetate tetrahydrate in 40 ml of acetic acid was heated to 80° C. in a Parr Hastelloy reactor with temperature and pressure transducer. After the temperature reached 80° C., 745 psi of $CO_2$ was introduced into the reactor, then 120 psi of $O_2$ was added slowly to the reactor. The mixture was stirred under pressure for six hours at 80° C., then the pressure was released, and the mixture was cooled to room temperature. The mixture solution was extracted with ethyl acetate then washed with a saturated NaCl solution in water and, dried over $Na_2SO_4$ to get adipic acid in 56% yield, with analyses by GC-MS and NMR. At 100 to 120° C., the yield was about 40 to 60% adipic acid.

Example 16

Oxidation of Cyclohexene Using CAT and NHSI

This reaction was performed with a solution of 0.1191 g (1.03 mmol) of N-hydroxysuccinimide, 2.0258 g (24.6 mmol) of cyclohexene and 0.1330 g (0.53 mmol) of cobalt acetate tetrahydrate in 40 ml of acetic acid was heated to 40° C. in a Parr Hastelloy reactor with temperature and pressure transducer. After the temperature reached 40° C., 745 psi of $CO_2$ was introduced into the reactor, then 120 psi of $O_2$ was added slowly to the reactor. The mixture was stirred under pressure for six hours at 40° C., then the pressure was released, and the mixture was cooled to room temperature. The mixture solution was extracted with ethyl acetate then washed with a saturated NaCl solution in water and, dried over $Na_2SO_4$ to give cyclohexanone, the major product 44% with 60% conversion analyzed by GC-MS. At 80° C., adipic acid was the major product.

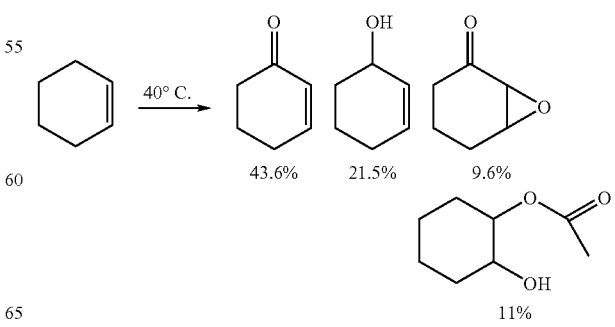

Example 16A

Oxidation of Cyclohexylbenzene Using CAT and NHSI

In this example, a solution of 0.1191 g (1.03 mmol) of N-hydroxysuccinimide, 1.1730 g (7.31 mmol) of cyclohexylbenzene and 0.1330 g (0.53 mmol) of cobalt acetate tetrahydrate in 40 ml of acetic acid was heated to 100° C. in a Parr Hastelloy reactor with temperature and pressure transducer. After the temperature reached 100° C., 745 psi of $CO_2$ was introduced into the reactor, then 120 psi of $O_2$ was added slowly to the reactor. The mixture was stirred under pressure for six hours at 100° C., then the pressure was released, and the mixture was cooled to room temperature. The mixture solution was extracted with ethyl acetate then washed with a saturated NaCl solution in water and, dried over $Na_2SO_4$ to yield pure white solid 5-benzoylvaleric acid (about 70% yield) after extraction by ethyl acetate with analyses by GC-MS and NMR.

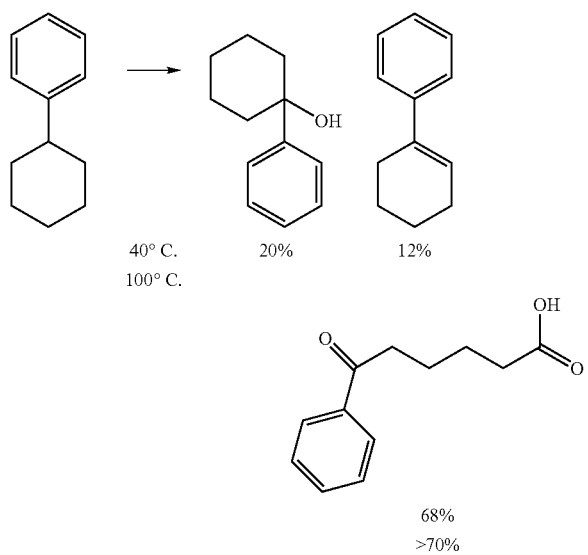

Example 16B

Oxidation of 1,2-Dimethylcyclopentane Using CAT and NHSI

In this example, a solution of 0.1191 g (1.03 mmol) of N-hydroxysuccinimide, 0.7074 g (7.20 mmol) of 1,2-dimethylcyclopentane and 0.1330 g (0.53 mmol) of cobalt acetate tetrahydrate in 40 ml of acetic acid was heated to 60° C. in a Parr Hastelloy reactor with temperature and pressure transducer. After the temperature reached 60° C., 745 psi of $CO_2$ was introduced into the reactor, then 120 psi of $O_2$ was added slowly to the reactor. The mixture was stirred under pressure for six hours at 60° C., then the pressure was released, and the mixture was cooled to room temperature. The mixture solution was extracted with ethyl acetate then washed with a saturated NaCl solution in water and, dried over $Na_2SO_4$ to yield pure oil 5-2,6-heptanedione (60% yield) after extraction by ethyl acetate with analyses by GC-MS and NMR.

Example 17

Oxidation of Cyclooctene Using CAT and NHSI

This reaction was performed with a solution of 0.1191 g (1.03 mmol) of N-hydroxysuccinimide, 2.0868 g (18.9 mmol) of cyclooctene and 0.1330 g (0.53 mmol) of cobalt acetate tetrahydrate in 40 ml of acetic acid was heated to 40° C. in a Parr Hastelloy reactor with temperature and pressure transducer. After the temperature reached 40° C., 745 psi of $CO_2$ was introduced into the reactor, then 120 psi of $O_2$ was added slowly to the reactor. The mixture was stirred under pressure for six hours at 40° C., then the pressure was released, and the mixture was cooled to room temperature. The mixture solution was extracted with ethyl acetate then washed with a saturated NaCl solution in water and, dried over $Na_2SO_4$ to give cyclooctene oxide, the only product 5% with 5% conversion analyzed by GC-MS.

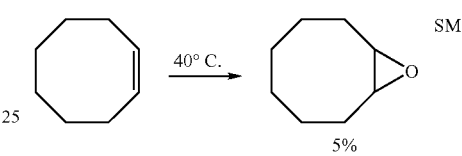

Example 18

Oxidation of 1-Phenyl-1-Cyclohexene Using CAT and NHSI

This reaction was performed with a solution of 0.1191 g (1.03 mmol) of N-hydroxysuccinimide, 1.0365 g (6.55 mmol) of 1-phenyl-1-cyclohexene and 0.1330 g (0.53 mmol) of cobalt acetate tetrahydrate in 40 ml of acetic acid was heated to 40° C. in a Parr Hastelloy reactor with temperature and pressure transducer. After the temperature reached 40° C., 745 psi of $CO_2$ was introduced into the reactor, then 120 psi of $O_2$ was added slowly to the reactor. The mixture was stirred under pressure for six hours at 40° C., then the pressure was released, and the mixture was cooled to room temperature. The solution was extracted with ethyl acetate then washed with a saturated NaCl solution in water and, dried over $Na_2SO_4$ to give the major product 95% 1-phenyl-2-acetate-1,2-cyclohexanediol analyzed by GC-MS.

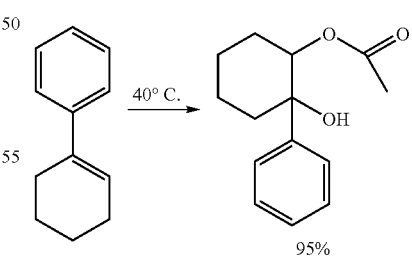

Example 19

Oxidation of Cyclooctene Using CAT and NHSI

This reaction was performed with a solution of 0.1191 g (1.03 mmol) of N-hydroxysuccinimide, 2.0357 g (18.5 mmol) of cyclohexene and 0.1330 g (0.53 mmol) of cobalt acetate tetrahydrate in 40 ml of acetic acid was heated to 100° C. in a Parr Hastelloy reactor with temperature and pressure transducer. After the temperature reached 100° C., 745 psi of CO$_2$ was introduced into the reactor, then 120 psi of O$_2$ was added slowly to the reactor. The mixture was stirred under pressure for one hour at 100° C., then the pressure was released, and the mixture was cooled to room temperature. The mixture solution was extracted with ethyl acetate then washed with a saturated NaCl solution in water and, dried over Na$_2$SO$_4$ to give 1,8-ocatane dioic 60% yield analyzed by NMR.

Example 20

Oxidation of 1-Methylcyclopentene Using CAT and NHSI

This reaction was performed with a solution of 0.1191 g (1.03 mmol) of N-hydroxysuccinimide, 2.0 g (24.3 mmol) of 1-methylcyclopentene and 0.1330 g (0.53 mmol) of cobalt acetate tetrahydrate in 40 ml of acetic acid was heated to 100° C. in a Parr Hastelloy reactor with temperature and pressure transducer. After the temperature reached 100° C., 745 psi of CO$_2$ was introduced into the reactor, then 120 psi of O$_2$ was added slowly to the reactor. The mixture was stirred under pressure for one hour at 100° C., then the pressure was released, and the mixture was cooled to room temperature. The solution was extracted with ethyl acetate then with a saturated NaCl solution in water and, dried over Na$_2$SO$_4$ to give, as the major 60% 5-ketohexanoic acid.

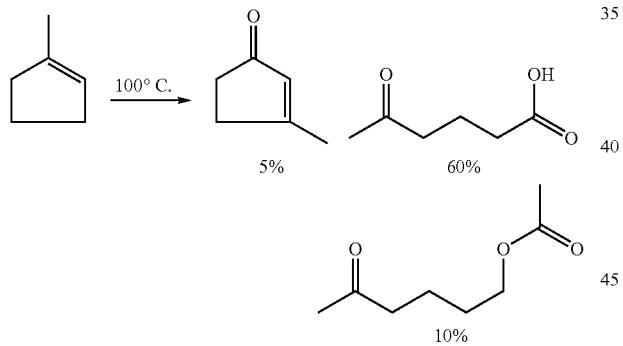

Example 20A

Oxidation of 1-Methylcyclohexene Using CAT and NHSI

In this example, a solution of 0.1191 g (1.03 mmol) of N-hydroxysuccinimide, 1.0493 g (10.9 mmol) of 1-methylcyclohexene and 0.1330 g (0.53 mmol) of cobalt acetate tetrahydrate in 40 ml of acetic acid was heated to 100° C. in a Parr Hastelloy reactor with temperature and pressure transducer. After the temperature reached 60° C., 745 psi of CO$_2$ was introduced into the reactor, then 120 psi of O$_2$ was added slowly to the reactor. The mixture was stirred under pressure for six hours at 60° C., then the pressure was released, and the mixture was cooled to room temperature. The mixture solution was extracted with ethyl acetate then washed with a saturated NaCl solution in water and dried over Na$_2$SO$_4$ to yield pure oil mixture after extraction by ethyl acetate with analysis by GC-MS and NMR.

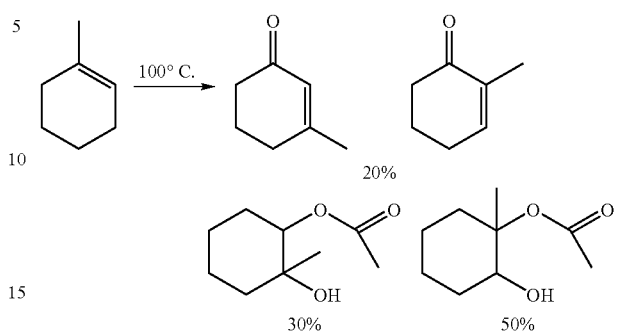

Example 21

Oxidation of p-Toluic Acid Using CAT and NHSI

In this example, a solution of 0.1208 g (1.05 mmol) of N-hydroxysuccinimide, (2.05 mmol) of p-toluic acid and 0.1142 g (0.46 mmol) of cobalt acetate tetrahydrate in 40 ml of acetic acid was heated to 25° C. in a Parr Hastelloy reactor with temperature and pressure transducer. After the temperature reached 25° C., 233 psi of air was slowly introduced into the reactor. The mixture was stirred under pressure for 24 hour at 25° C., then the pressure was released, and the mixture was cooled to room temperature (with oxidation time at 270 minutes). The white solid TPA was filtered, and the filtrate analyzed by HPLC using biphenyl as the internal standard. The solid TPA product was washed with acetic acid (20 ml) and dried in an oven at 120° C. for six hours to yield TPA 95%. At 21° C., the yield of TPA was about 90%.

Example 22

Oxidation of p-Tolualdehyde Using CAT and NHSI

In this example, a solution of 0.1208 g (1.05 mmol) of N-hydroxysuccinimide, 0.2123 g (1.77 mmol) of p-tolualdehyde and 0.1142 g (0.46 mmol) of cobalt acetate tetrahydrate in 40 ml of acetic acid was heated to 60° C. in a Parr Hastelloy reactor with temperature and pressure transducer. After the temperature reached 60° C., 233 psi of air was slowly introduced into the reactor. The mixture was stirred under pressure for one hour at 60° C., then the pressure was released, and the mixture was cooled to room temperature. A rapid temperature rise (due to heat generated by the exothermic oxidation) within roughly 20 minutes following O$_2$ introduction, accompanied by a drop in reactor pressure (due to consumption of O$_2$ in the liquid phase reaction) indicated rapid reaction. The white solid TPA was filtered, and the filtrate analyzed by HPLC using biphenyl as the internal standard. The solid TPA product was washed with acetic acid (20 ml) and dried in an oven at 120° C. for six hours to yield TPA (0.75 g, 98%).

Example 23

Oxidation of p-Nitrotoluene Using CAT and NHSI

In this example, a solution of 0.1191 g (1.03 mmol) of N-hydroxysuccinimide, 0.5104 g (3.72 mmol) of p-nitrotoluene and 0.1330 g (0.53 mmol) of cobalt acetate tetrahydrate in 40 ml of acetic acid was heated to 50° C. in a Parr Hastelloy reactor with temperature and pressure transducer. After the temperature reached 50° C., 745 psi of $CO_2$ was introduced into the reactor, then 120 psi of $O_2$ was added slowly to the reactor. The mixture was stirred under pressure for one hour at 50° C., then the pressure was released, and the mixture was cooled to room temperature. The solution was extracted with ethyl acetate then washed with a saturated NaCl solution in water and, dried over $Na_2SO_4$ to yield pure white solid p-nitrobenzoic acid (90% yield) after extraction by ethyl acetate with analyses by GC-MS and NMR.

Example 24

Oxidation of 4-Methylbenzyl Alcohol Using CAT and NHSI

In this example, a solution of 0.1456 g (1.26 mmol) of N-hydroxysuccinimide, 0.089 g (0.73 mmol) of 4-methylbenzyl alcohol and 0.1509 g (0.61 mmol) of cobalt acetate tetrahydrate in 40 ml of acetic acid was kept to 22° C. in a Parr Hastelloy reactor with temperature and pressure transducer. After the temperature reached 22° C., 745 psi of $CO_2$ was introduced into the reactor, then 120 psi of $O_2$ was added slowly to the reactor. The mixture was stirred under pressure for 24 hours at 22° C., then the pressure was released, and the mixture was cooled to room temperature. The white solid TPA was filtered, and the filtrate analyzed by HPLC using biphenyl as the internal standard. The solid TPA product was washed with acetic acid (20 ml) and dried in an oven at 120° C. for six hours to yield pure white solid terephthalic acid (96% yield).

Example 25

Catalyst Effect

In this example, the effect on xylene conversion and TPA yield was investigated with different cobalt catalysts. The reaction mixture comprised p-xylene, 0.13 M, NHSI, 0.0246 M, reacting at 50° C., $CO_2$ expanded acetic acid. The results shown in Table I are based on HPLC analysis.

TABLE 1

Effect of Catalyst of Yield and Conversion

| Condition* | Cobalt | Cobalt conc. | TPA yield | Xylene conversion |
|---|---|---|---|---|
| 50° C., $CO_2/O_2$ | Cobalt acetate | 2.17E−02 | 89.20% | >93% |
| 50° C., $CO_2/O_2$ | Cobalt acetate tetrahydrate | 2.32E−02 | 88.1% | >93% |
| 21° C., 1 atm | Cosalen | 4.66E−03 | <10% | <20% |
| 50° C., $CO_2/O_2$ | Co(acac)2 | 7.58E−3 | 73.9% | >93% |

*$O_2$ pressure at 100 psi and $CO_2$ pressure at 300 psi

Example 26

Temperature Effect

In this example, the effect of temperature on yield was investigated. The reaction comprised p-xylene 0.32 mol/L, $Co(OAc)_2$ $1.01\times10^{-2}$ mol/L, NHSI $2.1\times10^{-2}$ mol/L oxygen, 30 ml acetic acid in a 50 ml Parr Hastelloy reactor for six hours. The results are in Table 2.

TABLE 2

Effect of Temperature

| Temperature | TPA (round off) | CBA | PTA (ditto) |
|---|---|---|---|
| 25° C. | 79.77% | 7.42% | 12.80% |
| 50° C. | 86.76% | 3.74% | 9.50% |
| 60° C. | 96.42% | 0.77% | 2.81% |
| 100° C. | 97.66% | 2.04% | 0.30% |
| 110° C. | 98.12% | 0.67% | 1.22% |
| 120° C. | 98.82% | 0.74% | 0.44% |
| 125° C. | 94.00% | 2.12% | 3.87% |

Example 27

Oxidation Induction Time

The OIT is a matter of interest and the rapid reaction that follows that time interval could under some conditions represent a run-away reaction form 74 minutes to 145 minutes, depending on the relative initial partial pressure of $O_2$ and $CO_2$. Note that without $CO_2$, the OIT is greater with either $O_2$ or air, which implies that pressure of $CO_2$ may enhance $O_2$ availability in the liquid phase.

In this example, the effect of oxygen pressure on the TPA yield and induction time was investigated. The reaction mixture comprised p-xylene, $1.14\times10^{-3}$ mol, Co, $5.62\times10^{-4}$ mol, NHSI, $1.01\times10^{-3}$ mol, in 40 mL of acetic acid, reaction temperature, 22° C.

TABLE 3

Induction Times for Different Oxygen Pressures

| Oxygen pressure, psi | TPA yield, % | OIT, mins |
|---|---|---|
| 170 ($CO_2$, 260 psi) | 66.2 | 87.9 |
| 50 ($CO_2$, 260 psi) | 61.8 | 145.6 |
| 38 ($CO_2$, 356 psi) | 59.8 | 74.6 |

In a separate set of experiments, oxidation was performed at 50° C. in 30 ml of acetic acid with NHSI/Co [2/1] with [Co]=$1.01\times10^{-2}$ M, and 0.447 g of p-xylene. The results are shown in the following table, as well as FIG. 1.

TABLE 4

Oxidation of Toluene as a Function of Volumetric Expansion

| OIT (min) | Oxygen, psi | $CO_2$, psi | TPA yield |
|---|---|---|---|
| 46 | 240 | 0 | 87.9 |
| 16 | 180 | 350 | 75.3 |
| 29 | 200 | 210 | 81.0 |

Further, in this example, the effect of volumetric expansion on the TPA yield and induction time was investigated. The reaction mixture comprised p-xylene, $1.14\times10^{-3}$ mol, Co, $5.62\times10^{-4}$ mol, NHSI, $1.01\times10^{-3}$ mol, in 40 mL of acetic acid, reaction temperature, 22° C.

TABLE 5

Induction times at Different Oxygen Conditions

| pressure, psi | TPA yield, % | purity of TPA, % | OIT, mins |
|---|---|---|---|
| $O_2$, 90 ($CO_2$, 360 psi) | 63.8 | 92 | 170 |

TABLE 5-continued

Induction times at Different Oxygen Conditions

| pressure, psi | TPA yield, % | purity of TPA, % | OIT, mins |
|---|---|---|---|
| $O_2$, 120 | 83.9 | 90 | 289 |
| Air, 464 | 77.8 | 88.4 | 369 |

Example 28

Effect of Carbon Dioxide Volumetric Expansion on TPA Yield

In a separate experiment, catalytic oxidations in $CO_2$ expanded acetic acid were explored to show how the product yields change with different $CO_2$ pressures at 200 psi oxygen. Oxidation product yields of p-xylene varied with different mixtures of reaction media. Note that without $CO_2$, the oxidation induction time (OIT) is greater than with $CO_2$ using either 0 or air, which implies that the pressure of CO may enhance liquid phase. The reaction mixture comprised p-xylene, $1.14 \times 10^{-3}$ mol, Co, $5.62 \times 10^{-4}$ mol, NHSI, $1.01 \times 10^{-3}$ mol, in 40 mL of acetic acid. The results are shown in Table 6.

TABLE 6 p-xylene oxidation in $CO_2$ expanded acetic acid at 50° C.

| $N_2$, psi | $CO_2$, psi | TPA yield |
|---|---|---|
| 0 | 410 | 54 |
| 0 | 210 | 81 |
| 0 | 800 | 76 |
| 800 | 300 | 66 |
| 800 | 0 | 91 |
| 800 | 190 | 64 |
| 800 | 190 | 52 |
| 800 | 300 | 41 |

The following references are incorporated by reference.

REFERENCES

Cincotti et al., *Effect of catalyst concentration and simulation of precipitation processes on liquid-phase catalytic oxidation of p-xylene to terephthalic acid*, Chemical Engineering Science 52 (21/22), 4205-4213 (1997).
Hirai et al., *Oxidation of substituted toluenes with molecular oxygen in the presence of N,N',N-trihydroxyisocyanuric acid as a key catalyst*, Org. Chem. 68 (17), 6587-6590 (2003).
Ishii et al., *Innovation of Hydrocarbon Oxidation with Molecular Oxygen and Related Reactions*, Adv. Synth. Catal. 343 393-427 (2001).
Ishii et al., "Process for Production Aromatic Hydroxycarboxylic Acid Derivatives," U.S. Pat. No. 6,020,522, Issued May 11, 1998.
Jacob, R. C.; Varkery, P. S.; Rantnasamy, P., Applied Catal. A: General, 182, 91-96 (1999).
June et al., U.S. Pat. No. 6,153,790 for "Manufacture of aromatic dicarboxylic acids using cobalt and zirconium catalysts," issued Nov. 28, 2000.
Ming et al., *CO2-expanded Solvents: Unique and Versatile Media for Performing Homogeneous Catalytic Oxidations*, J. Am. Chem. Soc., 124 2513-17 (2002).
Ming et al., U.S. Pat. No. 6,448,454 for "Homogenous Catalytic Oxidation of Substrates in Organic Media Expanded by Dense Carbon Dioxide," Issued September 2002.
Musie et al., *Autoxidation of Substituted Phenols Catalyzed by Cobalt Schiff Base Complexes in Supercritical Carbon Dioxide*, Inorg. Chem. 40 3336-41 (2001).
Nakano et al., U.S. Pat. No. 5,958,821 for "Oxidation catalytic system and oxidation process using the same," Issued February 1997.
Parshall et al., *Homogeneous Catalysis*, John Wiley & Sons: New York, (1992).
Partenheimer, *Catal. Today,* 23, 69 (1995).
Raghavendrchar et al., Ind Eng Chem Res, 31, 453 (1992)
Sheehan, *Ullmann's Encyclopedia Industrial Organic Chemicals*, 8, 4573 (1999).
Subramaniam et al.; U.S. Pat. No. 6,740,785 for "Catalytic Oxidation of Organic Substrates by Transition Metal Complexes in Organic Solvent Media Expanded by Dense Carbon Dioxide," Issued May 25, 2004.

From the foregoing it will be seen that this invention is one well adapted to attain all ends and objectives herein-above set forth, together with the other advantages which are obvious and which are inherent to the invention. Since many possible embodiments may be made of the invention without departing from the scope thereof, it is to be understood that all matters herein set forth or shown in the accompanying drawings are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A process for oxidizing a substrate to a dicarboxylic acid comprising the steps of:
    forming a reaction mixture comprising
        an organic solvent system;
        an oxidizable substrate solubilized or dispersed in said solvent system, said oxidizable substrate selected from the group consisting, of o-xylene, m-xylene, and p-xylene or mixtures thereof; and
        an oxidation catalyst system solubilized or dispersed in said solvent system,
    introducing a sufficient quantity of compressed gas into said reaction mixture in order to volumetrically expand said reaction mixutre;
    introducing an oxidizing agent into said reaction mixture, thereby causing said oxidizable substrate to be oxidized;
    wherein said oxidation catalyst system comprises a cobalt carboxylate catalyst and a co-catalyst selected from the group consisting of N-hydroxysuccinimide;
    wherein said reaction mixture is maintained at a temperature less than about 125° C. when said oxidizing agent is initially introduced.

2. The process of claim 1 wherein said cobalt catalyst comprises a cobalt carboxylate selected from the group consisting of cobalt acetate tetrahydrate or anhydrous cobalt acetate, cobalt naphthenate, cobalt propionate, cobalt stearate and cobalt octanoate and their hydrous and anhydrous forms.

3. The process of claim 1 wherein said oxidizing agent is molecular oxygen.

4. The process of claim 1 wherein said reaction mixture is maintained at a temperature between about 20° C. and 100° C. when said oxidizing, agent is initially introduced.

5. The process of claim 1 wherein said reaction mixture is maintained at a temperature between about 20°° C. and 30° C. when said oxidizing agent is initially introduced.

6. The process of claim 1 wherein said oxidation occurs at a pressure between about 10 and 100 bar.

7. The process of claim 1 wherein said process has an induction period between about 30 minutes to 10 hours.

8. The process of claim 1 wherein said substrate is o-xylene.

9. The process of claim 1, wherein said substrate is m-xylene.

10. The process of claim 1, wherein said substrate is p-xylene.

11. The process of claim 1, wherein said organic solvent system is selected from the group consisting of acetic acid, propionic acid, chloroacetic acid, dichloroacetic acid, trichloroacetic acid, and trifluoroacetic acid.

12. The process of claim 1 wherein said reaction mixture is maintained at a temperature between about 20° C. and 80° C. when said oxidizing agent is initially introduced.

13. The process of claim 1 wherein the initial temperature of the reaction mixture is less than about 70° C. when said oxidizing agent is initially introduced.

14. The process of claim 1 wherein the initial temperature of the reaction mixture is less than about 60° C. when said oxidizing agent is initially introduced.

15. The process of claim 1 wherein the initial temperature of the reaction mixture is less than about 40° C. when said oxidizing agent is initially introduced.

16. The process of claim 1 wherein the initial temperature of the reaction mixture is less than about 30° C. when said oxidizing agent is initially introduced.

17. The process of claim 1 wherein said compressed gas is selected from the group consisting of carbon dioxide and air.

* * * * *